US012578266B2

(12) United States Patent (10) Patent No.: US 12,578,266 B2
Reimann et al. (45) Date of Patent: Mar. 17, 2026

(54) METHOD FOR PREDICTING A FEEDSTUFF AND/OR FEEDSTUFF RAW MATERIAL

(71) Applicant: Evonik Operations GmbH, Essen (DE)

(72) Inventors: Ingolf Reimann, Reinheim (DE); Joachim Reising, Kleinostheim (DE); Christoph Müller, Offenbach am Main (DE)

(73) Assignee: Evonik Operations GmbH, Essen (DE)

( * ) Notice: Subject to any disclaimer, the term of this patent is extended or adjusted under 35 U.S.C. 154(b) by 315 days.

(21) Appl. No.: 17/621,964

(22) PCT Filed: Jun. 23, 2020

(86) PCT No.: PCT/EP2020/067422
    § 371 (c)(1),
    (2) Date: Dec. 22, 2021

(87) PCT Pub. No.: WO2020/260234
    PCT Pub. Date: Dec. 30, 2020

(65) Prior Publication Data
    US 2022/0244173 A1     Aug. 4, 2022

(30) Foreign Application Priority Data
    Jun. 24, 2019    (EP) ..................................... 19181948

(51) Int. Cl.
    *G01N 21/35*     (2014.01)
    *A23K 40/00*     (2016.01)
    *G01N 33/02*     (2006.01)
(52) U.S. Cl.
    CPC ............. *G01N 21/35* (2013.01); *A23K 40/00* (2016.05); *G01N 33/02* (2013.01)

(58) Field of Classification Search
    CPC .............................. G01N 21/35; G01N 21/359
    See application file for complete search history.

(56) References Cited

U.S. PATENT DOCUMENTS

2016/0259792 A1     9/2016   Nedwed et al.

FOREIGN PATENT DOCUMENTS

WO     WO 2016/141198 A1     9/2016

OTHER PUBLICATIONS

Loudermilk et al., "Novel Search Algorithms for a Mid-Infrared Spectral Library of Cotton Contaminant", Applied Spectroscopy, vol. 62, No. 6. (Year: 2008).*

(Continued)

*Primary Examiner* — Casey Bryant
(74) *Attorney, Agent, or Firm* — Oblon, McClelland, Maier & Neustadt, L.L.P.

(57)     ABSTRACT

A computer-implemented method for predicting a feedstuff and/or feedstuff raw material is described. The method comprises providing a near infrared (NIR) spectrum of a sample of an unknown feedstuff raw material and/or feedstuff. The absorption intensities of wavelengths or wavenumbers in the spectrum are transformed to give a query vector. A set of database vectors of a population of spectra of known feedstuff raw materials and/or feedstuffs is also provided, and these comprise at least 50 spectra of samples of each feedstuff and/or feedstuff raw material from each of its global growing areas. The similarity between the query vector and each of database vectors is analyzed to produce a score, and the feedstuff raw material and/or feedstuff of the database vector with the highest score is assigned to the sample.

8 Claims, 1 Drawing Sheet

(56) References Cited

OTHER PUBLICATIONS

Yang et al., "Obtaining information about protein secondary structures in aqueous solution using Fourier transform IR spectroscopy", Nature Protocols vol. 10, pp. 382-396. (Year: 2015).*

International Search Report and Written Opinion issued Jul. 22, 2020 in PCT/EP2020/067422, filed on Jun. 23, 2020, 15 pages.

Extended European Search Report issued on Dec. 9, 2019 in European Patent Application No. 19181948.1 filed Jun. 24, 2019, 13 pages.

Reeves III et al. "Spectral Library Searching: Mid-Infrared Versus Near-Infrared Spectra for Classification of Powdered Food Ingredient", Applied Spectroscopy, The Society for Applied Spectroscopy, vol. 53, No. 7, Jul. 1999, pp. 836-844.

Chu et al. "Algorithms, Strategies and Application Progress of Spectral Searching Methods", Chinese Journal of Analytical Chemistry, vol. 42, No. 9, Sep. 2014, pp. 1379-1386.

Loudermilk et al. "Novel Search Algorithms for a Mid-Infrared Spectral Library of Cotton Contaminants", Applied Spectroscopy, vol. 62, No. 6, Jun. 2008, pp. 661-670.

Osborne "Near-infrared Spectroscopy in Food Analysis", Meyers R A & McGorrin R J; Encyclopedia of Analytical Chemistry, 2006, 14 pages.

U.S. Appl. No. 17/758,994, filed Jul. 18, 2022, Reimann, et al.

U.S. Appl. No. 17/768,431, filed Apr. 12, 2022, Reimann, et al.

Peng et al., "Study on SVM Calibration Model Parameter for Mixed Gas," Advanced in Control Engineering and Information Science, SciVerse ScienceDirect, Procedia Engineering 15 3642-3645 Air Force Engineering University, Science Institute, (2011).

* cited by examiner

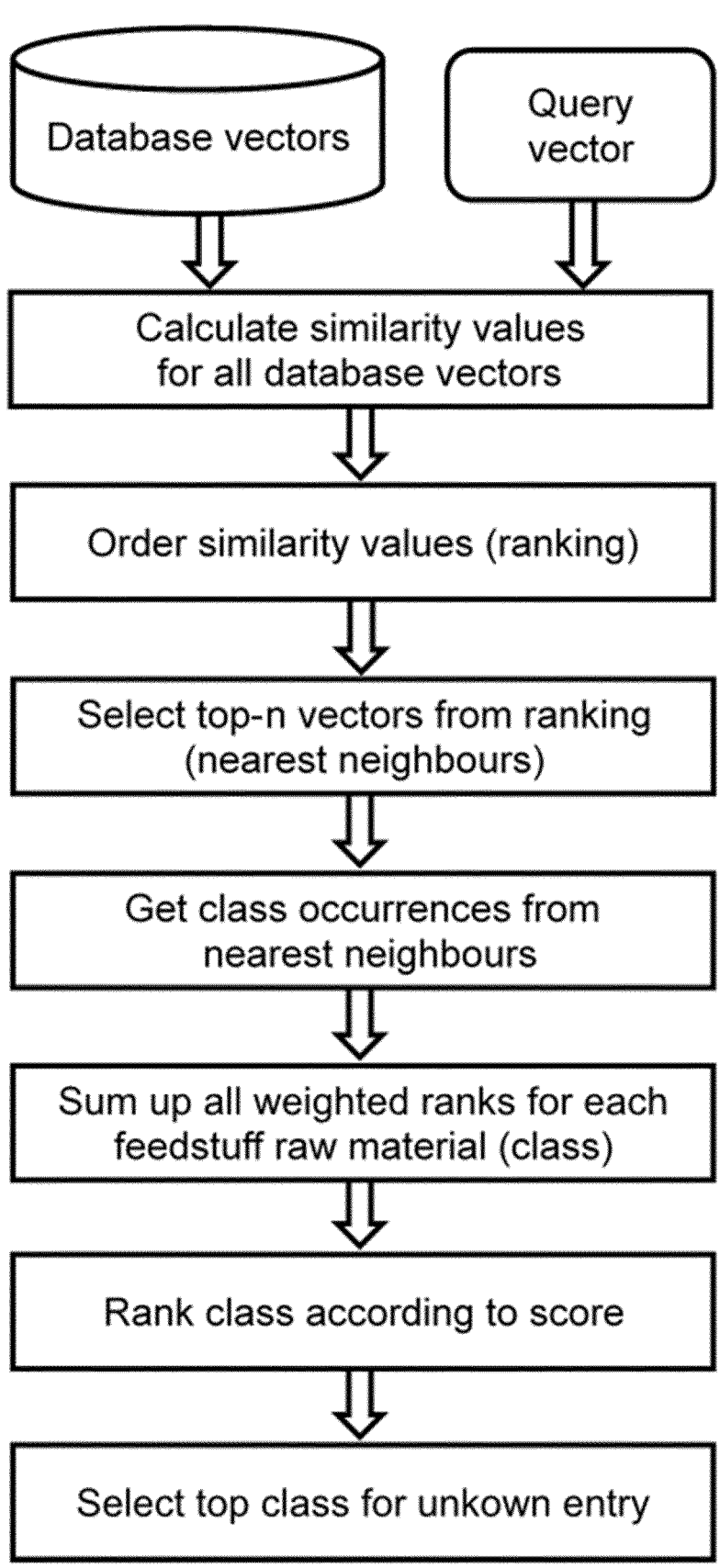

METHOD FOR PREDICTING A FEEDSTUFF AND/OR FEEDSTUFF RAW MATERIAL

The present invention relates to a method for predicting a feedstuff raw material and/or feedstuff of unknown type by means of near infrared spectroscopy and similarity analysis.

Animal diets typically contain a variety of different feedstuffs and/or feedstuff raw materials. It is therefore necessary to know the identity and type of a feedstuff and/or feedstuff raw material as precisely and as quickly as possible. This is relevant, in particular, when different feedstuffs and/or feedstuff raw materials shall be mixed to yield a diet with a specific composition for a specific species. The methods of qualitative analysis of feedstuffs and feedstuff raw materials in principle allow a precise identification of feedstuffs and/or feedstuff raw materials of unknown type, i.e. unknown identity, origin etc. However, these methods require cost- and maintenance-intensive lab equipment. Further disadvantages of these methods are their high standards for the time required and the expertise and experience of the operating staff. In principle, near infrared spectroscopy would be a suitable means for the identification and determination of feedstuffs and/or feedstuff raw materials. The article "Near-infrared Spectroscopy in Food Analysis" (Osborne B. G., Encyclopedia of Analytical Chemistry, Wiley & Sons, 2006, pages 1-14) gives an overview over the application of near infrared (NIR) spectroscopy in this field. According to this article the wide range of applications of NIR in food analysis is possible because of the different sample presentation techniques. There is a technique available for any type of liquid, slurry, powdered or solid sample. When used as a routine method, however, near infrared spectroscopy requires the knowledge of the identity and type of feedstuffs and/or feedstuff raw materials. However, human mistakes in the selection of feedstuffs and/or feedstuff raw materials can already lead to an incorrect classification of a feedstuff and/or feedstuff raw material regarding its identity and present form. Based on incorrect classification, the wrong calibration method would be chosen for the near infrared analysis of the ingredients and their specific amounts in the feedstuff and/or feedstuff raw material. Thus, the data obtained from the incorrectly calibrated NIR spectrometer would be erroneous. Consequently, these data would be misleading for any further operating steps, in which the respective feedstuff raw material and/or feedstuff is involved.

An option to overcome this problem is to perform a similarity analysis of the near infrared spectrum of a sample substance with reference spectra to identify matches, thereby determining what the sample substance is. The general principle of this approach is described in WO 2016/141198 A1 and in the article "Algorithms, Strategies and Application Process of Spectral Searching Methods" (Chu X.-L., Li J.-Y., Chen P., Xu Y.-P., Chinese Journal of Analytical Chemistry, 2014, 42(9), 1379-1386). In detail, a similarity analysis involves the calculation of a similarity measure or a distance measure between the spectrum of the sample substance and the reference spectra. A high value for the similarity measure between the sample spectrum and a reference spectrum indicates a high similarity of a sample substance with the reference substance of the respective reference spectrum. By comparison, when the similarity analysis involves a distance measure, a low similarity value indicates a high similarity of a sample substance to the reference substance of the respective reference spectrum. The similarity values obtained in a similarity analysis are typically ranked with the reference substances of the top-ranked entries having the greatest similarity with the sample substance.

The article "Spectral Library Searching: Mid-Infrared Versus Near-Infrared Spectra for Classification of Powdered Food Ingredient" (Reeves J. B. et al., Applied Spectroscopy, 1999, vol. 53, no. 7, pages 836-844) discloses a method for predicting a food ingredient comprising the steps of providing near infrared (NIR) spectra of samples of powdered food ingredients, libraries of spectra were constructed and searched on the basis of full spectrum algorithms. The results for the various searches are presented as distances between the unknown or test sample and samples in the library of the algorithms in question. A match was considered to be successful when the nearest sample (smallest distance) to a test sample was for a sample from the same group.

However, the approaches of the prior art are very susceptible to false determinations or predictions when false positive entries are at the top of the ranking of similarity values. Reasons for false positive entries in said ranking can be the erroneous assignment of a spectrum to the wrong reference substance or wrong class of references substances, the heterogeneity or messiness of a class of references substances, whose spectra were recorded, or the similarity of some reference substances to one another, which makes an exact matching rather difficult. Any of these cases make it difficult or impossible to precisely and reliably match the sample spectrum of a sample substance to the spectrum of a reference substance.

The article "Novel Search Algorithms for a Mid-Infrared Spectral Library of Cotton Contaminants" (Loudermilk J. B. et al, Applied Spectroscopy, June 2008, vol. 62, no. 6, pages 661-670) discloses voting scheme algorithms used in MIR library search of cotton contaminants. A counting is done in the so-called "group" algorithm, e.g. the number of times the substance/category "seed coat" is occurring in a hit list. A weighting according to rank, followed by summation to result in a score, is done the "weighted frequency" algorithm, for single spectra and their occurrence in hit lists of multiple search algorithms. Said "weighted frequency" algorithm therefore works with multiple search algorithms for a single spectrum.

According to the present invention this problem is solved in that first a similarity analysis is performed, followed by counting the occurrences of a feedstuff raw material and/or feedstuff in the ranking of similarity values. Next, the thus determined number of similarity values of the feedstuff raw material and/or feedstuff are weighted according to their rank position to give weighted rank position, the sum is formed of the weighted rank positions to give scores of the feedstuff raw materials and/or feedstuffs, and the highest score indicates the feedstuff raw material and/or feedstuff with the greatest similarity to the sample substance.

Object of the present invention is therefore a computer-implemented method for predicting a feedstuff and/or feedstuff raw material comprising the steps of a) providing a near infrared (NIR) spectrum of a sample of an unknown feedstuff raw material and/or feedstuff, b) transforming absorption intensities of wavelengths or wavenumbers in the spectrum of step a) to give a query vector, c) providing a set of database vectors of a population of spectra of known feedstuff raw materials and/or feedstuffs, wherein the population of spectra of known feedstuffs and/or feedstuff raw materials of step c)

comprises at least 50 spectra of samples of each feed-stuff and/or feedstuff raw material from each of its global growing areas, d) analyzing the similarity between the query vector of step b) and the set of database vectors of step c) comprising the steps d1) calculating a similarity measure and/or a distance measure between each database vector of step c) and the query vector of step b) to give a similarity value for each database vector with the query vector, d2) ranking the similarity values obtained in step d1) in descending order, when the similarity measure is calculated in step d1) or in ascending order, when the distance measure is calculated in step d1), wherein the top-ranked database vector has the greatest simi-larity with the query vector, d3) counting the number of occurrence of each of the feedstuff raw materials and/or feedstuffs among the top-ranked database vectors in the ranking of step d2), wherein said number of occurrences is indicated by the variable N, d4) weighting the first N similarity values of each of the feedstuff raw materials and/or feedstuffs according to their position in the ranking of step d2) to give weighted rank positions of each of the feedstuff raw materials and/or feedstuffs, d5) forming the sum of the weighted rank positions of step d4) for each of the feedstuff raw materials and/or feedstuffs to give scores of each of the feedstuff raw materials and/or feedstuffs, and e) assigning the feedstuff raw material and/or feedstuff of the database vector with the highest score to the sample of step a).

In the context of the present invention the term unknown feedstuff raw material and/or feedstuff refers to any kind of feedstuff and/or feedstuff raw material whose identity, com-position, origin and/or form, i.e. whether it is ground or unground, is not known. By comparison, in the context of the present invention the term known feedstuff raw material and/or feedstuff refers to any kind of feedstuff and/or feed-stuff raw material whose identify, composition, origin and/or form, i.e. whether it is ground or unground, is known. Accordingly, a population of spectra of known feedstuff raw materials and/or feedstuffs is a number or multitude of spectra, which are known to belong to a specific feedstuff and/or feedstuff raw material of known identity, composi-tion, origin and/or form.

The weighting of the similarity values in step d4) is typically done by taking the reciprocal rank position of the specific feedstuff raw material and/or feedstuff in the rank-ing of step d2). For example, if there is an occurrence of a specific feedstuff raw material at position 2 in the ranking, its weighing gives the value ½ for the weighted rank position. The first N similarity values of each of the feedstuff raw materials and/or feedstuffs are weighted according to their position in the ranking of step d2) to give weighted rank positions of each of the feedstuff raw materials and/or feedstuffs in step d4). Next, in step d5) the sum is formed of the weighted rank positions of step d4) for each of the feedstuff raw materials and/or feedstuffs to give scores of each of the feedstuff raw materials and/or feedstuffs.

In its broadest meaning a vector is a geometric object that has magnitude (or length) and direction. In a Cartesian coordinate system, a vector can be represented by identify-ing the coordinates of its initial and terminal point. There-fore, a vector is suited to represent an absorption intensity at a specific wavelength or wavenumber in a two-dimensional near infrared spectrum. In addition, a vector is not limited to the description of a two-dimensional system. Rather, a vector can describe multi-dimensional spaces, such as a near infrared spectrum with a multitude of absorption intensities at a multitude of different wavelengths or wavenumbers. In this case, each dimension of the said vector corresponds to a single absorption intensity at a specific wavelength or wavenumber. In the context of the present invention a database vector also contains the identification of its feed-stuff raw material and/or feedstuff and optionally, its origin, or other information, such as whether it is ground or unground, or the season when it was harvested, in case it is a corn. Alternatively, each database vector has an identifi-cation number and the information mentioned before are stored under the identification number on a processing unit, such as a computer, cloud, or server.

In one embodiment of the computer-implemented method according to the present invention the vector in steps b) and c) is a multi-dimensional vector, with each dimension cor-responding to an absorption intensity of a specific wave-length or wavenumber.

Like the query vector of the spectrum of an unknown feedstuff raw material and/or feedstuff, also the set of database vectors provided in step c) of the computer-imple-mented method according to the present invention is obtained by transforming each spectrum of a population of spectra of known feedstuff raw materials and/or feedstuffs into the corresponding vector. If the set of database vectors is not already present, the step c) also comprises the trans-formation of each spectrum of a population of spectra of known feedstuff raw materials and/or feedstuffs into the corresponding vector to give the set of database vectors. In that case the step c) of the computer-implemented method according to the present invention comprises the steps of transforming each spectrum of a population of spectra of known feedstuff raw materials and/or feedstuffs to the cor-responding vector to give a set of data set vectors and providing the thus obtained set of database vectors of a population of spectra of known feedstuff raw materials and/or feedstuffs.

According to the present invention a near infrared spec-trum of a sample of an unknown feedstuff raw material and/or feedstuff is provided in step a). In the context of the present invention this means that the place where the spec-trum to be provided is recorded and the place where the computer-implemented method according to the present invention is performed, can be different or identical. For example, it is possible that a near infrared spectrum of a sample of an unknown feedstuff raw material and/or feed-stuff is recorded at one place, and sent in any way to a remote place, where the computer-implemented method according to the present invention is performed. Alternatively, both recording of the spectrum and the prediction of the feedstuff raw material and/or feedstuff based on said spectrum can be performed at the same place.

In an embodiment the step a) of the computer-imple-mented method the step comprises the recording of a near infrared spectrum of a sample of an unknown feedstuff raw material and/or feedstuff.

In principle, the near infrared (NIR) spectrum of step a) can be recorded at wavelengths of from 700 to 2,500 nm with any suitable near infrared spectrometer working either on the monochromator or on the Fourier transform principle. However, it was found that only the part of near infrared spectra of from 1,100 to 2,500 nm is necessary for prediction of feedstuff raw material and/or feedstuff in the computer-implemented method according to the present invention. Therefore, it is preferred that the spectrum is recorded in the range of from 1,100 to 2,500 nm in step a) of the computer-implemented method according to the present invention. Accordingly, the population of spectra of known feedstuff raw materials and/or feedstuffs of step c) of the computer-implemented only needs to cover the range of from 1,100 to 2,500 nm. Since wavelengths are easily convertible into the respective wavenumbers, the near infrared spectrum of step a) and/or the spectra of step c) can also be recorded at the corresponding wavenumbers. When the sample of a feedstuff raw material and/or feedstuff in step a) is not translucent, the reflectance of the emitted light from the sample is measured and the difference between the emitted light and the reflected light is given as absorption. The thus obtained absorptions, i.e. their intensities and their wavelengths or wavenumbers, are used for the generation of the vectors in step b) and/or in step c). Accordingly, a near infrared spectrometer suitable for use in the method according to the present invention can work either in the transmittance mode or in the reflectance mode.

In an embodiment of the computer-implemented method according to the present invention the spectrum in step a) and/or in step c) is recorded in a range of from 1,100 to 2,500 nm.

The method according to the present invention is not limited to a specific distance or similarity measure for analyzing the similarity between the query vector of step b) and the database vectors of step c). Therefore, any distance or similarity measure, which is suited to determine the similarity of the vector of step b) with the vectors of step c) can be used in the method according to the present invention. In principle, a similarity analysis is based on a nearest neighbor search. It was found that the Cosine coefficient is a particularly suitable similarity measure for a nearest neighbor search in the method according to the present invention. For example, the Cosine coefficient, which allows the calculation of the similarity between two vectors extremely rapidly with a high precision, is particularly suitable for the method according to the present invention. The Cosine coefficient $S_{A,B}$ of two vectors A and B is represented by the following formula $$S_{A,B} = \frac{\left[\sum_{j=1}^{j=n} x_{jA} x_{jB}\right]}{\left[\sqrt{\sum_{j=1}^{j=n} (x_{jA})^2} \sqrt{\sum_{j=1}^{j=n} (x_{jB})^2}\right]}$$

where $x_{jA}$ and $x_{jB}$ are components of the vectors A and B, respectively, and n is the number of spaces, here the number of absorption intensities at specific wavelengths or wavenumbers. The values for the similarity range from −1, meaning exactly the opposite to each other, to 1, meaning identity, with 0 indicating orthogonality (decorrelation), and in-between values indicating intermediate similarity or dissimilarity.

Alternatively, the similarity between the vectors can be also be calculated by means of a distance measure. For example, the Euclidian distance, which also allows the calculation of the similarity between two vectors extremely rapidly and precisely, is particularly suitable for the method according to the present invention. The Euclidian distance $D_{A,B}$ of two vectors A and B is represented by the following formula $$D_{A,B} = \sqrt{\sum_{j=1}^{j=n} (x_{jA} - x_{jB})^2}$$

where $x_{jA}$ and $x_{jB}$ are components of the vectors A and B, respectively, and n is the number of spaces, here the number of absorption intensities at specific wavelengths or wavenumbers.

It is therefore preferred that in step d1) of the computer-implemented method according to the present invention the similarity measure is the Cosine coefficient and the distance measure is the Euclidian distance.

According to step b) of the present invention absorption intensities of wavelengths or wavenumbers in a spectrum are transformed to give a query vector. In principle, one could select the strongest and therefore most meaningful absorption intensities in a spectrum and transfer only said absorption intensities to give a vector. However, this would require a thorough analysis of each individual spectrum of a sample substance, which is not only time-consuming but also requires a very good understanding of near infrared spectra. Hence, this approach would not be suitable for a routine analysis. Further, this approach has the disadvantage that meaningful but relatively weak absorption intensities in a spectrum may be ignored so that information would get lost. This could lead to a wrong assigning of the unknown feedstuff raw material and/or feedstuff in the end. It is therefore favorable to consider as many information as possible in the spectrum without a preceding in-depth analysis of the spectrum. It is therefore preferred to transform the absorption intensities of equidistant wavelengths or wavenumbers in a spectrum, i.e. in step b) and/or c), to give a vector of said spectrum. In order to allow to the best possible similarity analysis between the query vector and the database vectors, it is preferred to transform the absorption intensities of equidistant wavelengths or wavenumbers in a spectrum of step b) and step c) of the method according to the present invention to give a vector of said spectrum or spectra. Preferably, the distances of the absorption intensities being transformed to vectors in step b) are identical with the distances of the absorptions intensities transformed to vectors in step c). This allows for a higher precision in the prediction of the computer-implemented method according to the present invention, even without having any specific knowledge of the sample substance and its spectra at all.

In an embodiment in step b) and/or step c) of the computer-implemented method according to the present invention the absorption intensities of equidistant wavelengths and/or wavenumbers in a spectrum are transformed to give a vector of a spectrum of step a) and/or of step b).

In a further embodiment of the computer-implemented method according to the present invention the distances of the absorption intensities being transformed to vectors in step b) are identical with the distances of the absorptions intensities transformed to vectors in step c).

Preferably, the absorption intensities of wavelengths or wavenumbers in a spectrum, which are transformed to give a vector of said spectrum, have small distances between each other. This has the advantage that most if not all relevant absorption intensities, i.e. information, of a spectrum are transformed to a vector of said spectrum. This is believed to allow a very precise transformation of all relevant information of a spectrum into vectors, even without having knowledge of the feedstuff and/or feedstuff raw material whose spectrum was recorded, in particular of its identity, composition, origin and/or form. Preferably, the distance between the wavelengths in step b) of the method according to the present invention is from 0.1+/−10% to 10+/−10% nm, from 0.1+/−10% to 5+/−10% nm, or from 0.1+/−10% to 2+/−10% nm. Accordingly, the distance between the wavenumbers in step b) of the method according to the present invention is from $10^8$+/−10% to $10^6$+/−10%, from $10^8$+/−10 to $5*10^6$+/−10% nm, or from $10^8$+/−10% to $2*10^6$+/−10% nm. In the context of the present invention, the term +/−10% is used with respect to explicitly mentioned values to indicate that deviations from said explicitly mentioned values are still within the scope of the present invention, provided that they essentially lead to the effects of the present invention. The distances between the wavelengths or wavenumbers in step c) of the method according to the present invention are preferably the same as those in step b), in order to provide for the best possible comparison between the recorded spectrum of an unknown feedstuff and/or feedstuff raw material and the spectra of known feedstuffs and/or feedstuff raw materials.

In an embodiment of the computer-implemented method according to the present invention, the distance between the wavelengths or wavenumbers in step b) and/or step c) is from 0.1 nm+/−10% to 10 nm+/−10% or from $10^8$ cm$^{-1}$+/−10% to $10^6$ cm$^{-1}$+/−10%.

In principle, the computer-implemented method according to the present invention is not subject to any limitation regarding the number of absorption intensities to be transformed to give a vector. Rather, the number of relevant information in a spectrum of a feedstuff raw material and/or feedstuff strongly depends on the individual feedstuff raw material and/or feedstuff, and in particular, on its composition and components. The more complex a feedstuff and/or feedstuff raw material is, i.e. the more components a feedstuff and/or feedstuff raw material contains, the more information are required from a near infrared spectrum for predicting an unknown feedstuff and/or feedstuff raw material. Again, it would not be practical to perform an in-depth analysis in order to find out the absorption intensities which necessarily must be transferred to give a vector. A suitable option for the number of absorption intensities to be transformed to give a vector is to correlate them with the distance between the corresponding wavelengths or wavenumbers, e.g. from 0.1 nm+/−10% to 10 nm+/−10% or 0.1+/−10% to 2+/−10% nm, and the recording range of the spectrum, e.g. from 1,100 to 2,500 nm. Preferably, the number of absorption intensities in each spectrum to be transformed into a vector is at least 100, in particular, said number ranges from 150+/−10% to 15,000+/−10% or from 700+/−10% to 15,000+/−10%.

In another embodiment of the method according to the present invention the number of absorption intensities in each spectrum being transformed to a vector is 100+/−10% or more.

In principle, the step d3) of the method according to the present invention is not subject to any limitations regarding the number of top-ranked vectors, apart from the number of entries in the ranking of step d2). However, the preciseness of the prediction in the method according to the present invention is neither affected when the step d3) involves the use of a relatively low number of database vectors nor is the preciseness improved in any way, when the step d3) involves the use of a relatively high number of database vectors. Rather, when d3) involved the use of a larger number of database vectors in the ranking of step d2), beyond the database vectors being really top-ranked, this would result in an increasing number of less meaningful database vectors, which would decrease the preciseness of prediction in the method according to the present invention. It is therefore preferred that the number N of the first top-ranked database vectors in step d3) ranges from 10 to 100, 10 to 90, 10 to 80, 10 to 70, 10 to 60, 10 to 50, 10 to 40, 10 to 30, or 10 to 20. This leads to very precise predictions equivalent to the use of a larger number of database vectors, however, without unnecessarily increasing the computing effort, as is the case for more database vectors.

In one embodiment of the method according to the present invention the number of the top-ranked database vectors to be considered in step d3) ranges from 10 to 100, preferably from 10 to 50.

The population of spectra of known feedstuff raw materials and/or feedstuffs used in the method according to the present invention is not limited to specific feedstuff raw materials and/or feedstuff. Rather, it preferably comprises spectra of all feedstuff raw materials and/or feedstuffs used in animal nutrition, preferably in the nutrition of poultry, pigs, pigs and/or animals kept in aquacultures, such as fish and/or crustacea. The spectra of the feedstuff raw materials and/or feedstuffs may significantly differ depending on their form or appearance, e.g. when they are present in ground or unground form. Therefore, the spectra population preferably also comprises spectra, which were recorded from the aforementioned feedstuff raw materials and/or feedstuff in ground and/or unground form.

In another embodiment of the method according to the present invention the population of spectra of known feedstuffs and/or feedstuff raw materials in step c) of said method comprises spectra of all feedstuffs and/or feedstuff raw materials in ground and/or unground form used in animal nutrition.

In principle, the method according to the present invention is not limited in any way regarding the number and types of feedstuffs and/or feedstuff raw materials, whose spectra, recorded in ground and/or unground form, make up the spectra population. Notwithstanding, it is preferred that the population of spectra of known feedstuffs and/or feedstuff raw materials in step c) of said method comprises spectra of all feedstuffs and/or feedstuff raw material in ground and/or unground form used in animal nutrition, preferably in the nutrition of poultry, pigs, pigs and/or animals kept in aquacultures, such as fish and/or crustacea The feedstuff raw material and/or feedstuff can be of animal and/or vegetable origin. Particularly preferred feedstuffs and/or feedstuff raw materials are unprocessed and/or processed feedstuff raw materials and/or feedstuff. Processed feedstuff raw materials and/or feedstuff are those, which were subjected to any type of heat or pressure treatment in order to remove or detoxify anti-nutritive factors. Preferred feedstuffs and/or feedstuff raw material are oilseeds, in particular soy extraction meal and expeller, full-fat soybeans, rapeseed meal and expeller, cotton extraction meal, peanut extraction meal, sunflower extraction meal, coconut extraction meal, and/or palm kernel extraction meal; legumes, in particular toasted guar flour; brewery and distillation by-products, in particular dried distiller's grain with solubles (DDGS), by-products of grain-processing and feedstuff production, in particular corn gluten, maize seed meal and/or bakery by-products; anima by-products, in particular fish meal, meat meal, poultry meal, blood meal, and/or bone meal; and also any type of grains. In particular, the feedstuff raw material is soy, soybeans or a soybean product.

Depending on factors such as climate, soil and genetics of the plants, feedstuff raw materials and/or feedstuff from different global growing areas may differ in their ingredients and the contents of said ingredients. In order to allow for reliable and reproducible predictions of a feedstuff and/or feedstuff raw materials, therefore the feedstuff raw material and/or feedstuff, whose spectra are part of the spectra population, is from all of its global growing areas.

The number of spectra of feedstuff raw materials and/or feedstuffs of the spectra population used in the method according to the present invention should be representative to allow for a reliable and reproducible prediction of the feedstuff raw material and/or feedstuff in question. Therefore, the population of spectra comprises at least 50 spectra of samples of each feedstuff and/or feedstuff raw material, i.e. each feedstuff and/or feedstuff raw material in ground and/or unground form used in animal nutrition, preferably in the nutrition of poultry, pigs, pigs and/or animals kept in aquacultures, such as fish and/or crustacea, from each of its global growing areas. The method according to the present invention is not subject to any limitations regarding the number of spectra of samples of any feedstuff and/or feedstuff raw material from any of its global growing areas. Hence, the number of spectra of samples of any feedstuff and/or feedstuff raw material from any of its global growing areas may range from 50 to 10,000, from 50 to 5,000, from 50 to 2,500, from 50 to 2,000, from 50 to 1,500, from 50 to 1,000, from 100 to 1,000, from 50 to 500, from 100 to 500, from 50 to 250, from 100 to 250, or from 50 to 100.

When the population of spectra of feedstuffs and/or feedstuff raw material of known type considers each global growing area of a feedstuff and/or feedstuff raw material and the number of spectra from each global growing area is representative, the method according to the present invention allows not only a reliable and reproducible prediction of the feedstuff raw material and/or feedstuff in question but also a prediction of the origin of the feedstuff raw material and/or feedstuff in question.

Therefore, said population of spectra of known feedstuffs and/or feedstuff raw material of step c) preferably comprises at least 50 spectra of samples of each feedstuff and/or feedstuff raw material from each of its global growing areas. The number of spectra of samples of a feedstuff and/or feedstuff raw material from each global growing area is not subject to any limitations. Hence, the number of spectra of samples of any feedstuff and/or feedstuff raw material from each global growing area may range from 50 to 10,000, from 50 to 5,000, from 50 to 2,500, from 50 to 2,000, from 50 to 1,500, from 50 to 1,000, from 100 to 1,000, from 50 to 500, from 100 to 500, from 50 to 250, from 100 to 250, or from 50 to 100.

The population of spectra of known feedstuffs and/or feedstuff raw material may be an already existing database, preferably a constantly updated database, and/or it may be a new database, which is constantly updated or further developed. A database of spectra of feedstuffs and/or feedstuff raw material of known type suited for use in the method according to the present invention is for example Evonik's AMI-NODat® 5.0.

Cases may arise, where the position of a signal peak in a spectrum, either in step b) and/or in step c) of the method according to the present invention cannot be located because the maxima and minima of the individual peaks cannot be clearly identified in such a spectrum. An easier locating of individual peaks in the spectrum is possible, when the minima and maxima of the peaks are easier identifiable. Taking the first derivative of a spectrum facilitates the identification of the peaks in the spectrum because it gives a zero crossing of peak maxima or peak minima. Taking the second derivative gives a peak minimum at exactly that position, where a peak maximum was in the original spectrum and vice versa. Taking the first or second derivative of a spectrum also facilitates the identification of an outlier in the population of spectra of known feedstuff raw materials and/or feedstuffs.

In another embodiment of the method according to the present invention a derivative of the spectrum of the unknown feedstuff raw material and/or feedstuff of step a) and/or of the spectra of known feedstuff raw materials and/or feedstuffs of step c) is/are formed.

Preferably, the first derivative of the spectrum of a feedstuff and/or feedstuff raw material of unknown type of step a) and/or of the spectra of known feedstuffs and/or feedstuff raw materials of step c) is/are formed.

It is preferred to provide the set of database vectors of a population of spectra of known feedstuff raw materials and/or feedstuffs directly in step c) of the computer-implemented method according to the present invention. Notwithstanding, it is also possible that first only a population of spectra of known feedstuff raw materials and/or feedstuffs is provided, which is transformed in the next step to the set of database vector for the similarity analysis in step d). In this case, the step c) of the computer-implemented method according to the present invention also comprises the step of transforming the absorption intensities of wavelengths or wavenumbers in each spectrum of a population of spectra of known feedstuff raw materials and/or feedstuffs into vectors. The thus obtained multitude of vectors of the population of spectra of known feedstuff raw materials and/or feedstuffs is then the set of database vectors, as mentioned above. In any case, it is preferred to store the population of spectra of known feedstuff raw materials and/or feedstuffs or the set of database vectors of said population of spectra of known feedstuff raw materials and/or feedstuffs on a processing unit, such as a computer or a cloud. The processing unit on which the population of spectra or the database vectors are stored can be identical with or different from the processing unit, which carries out the computer-implemented method according to the present invention. In the second case, the first processing unit, which carries out the computer-implemented method according to the present invention, and the second processing unit, on which the population of spectra or the database vectors are stored, form a network. For example, it is also possible that the population of spectra or the database vectors are stored on a cloud. In that case, the first processing unit, e.g. a computer, which carries out the computer-implemented method according to the present invention, and the second processing unit, e.g. a cloud, on which the population of spectra or the database vectors are stored, form a network.

Another object of the present invention is therefore a system for predicting a feedstuff raw material and/or feedstuff, comprising i) a processing unit adapted to carry out the computer-implemented method according to the present invention.

In case the population of spectra of known feedstuff raw materials is stored on a computer, it is preferred that said population is stored on a second computer, i.e. a computer, which does not already carry out the computer-implemented method according to the present invention. As consequence, the working load is evenly distributed between the computers, which may lead to a quicker performance of the computer-implemented method according to the present invention. This also allows for a communication between the user and the provider of a database with the database vector for use in the method according to the present invention, for example, an update of the database vectors.

In an embodiment of the system according to the present invention the processing unit adapted to carry out the computer-implemented method according to the present invention forms a network with at least one other processing unit, on which the database vectors are stored.

DESCRIPTION OF THE FIGURE

FIG. 1 is a representation of the computer-implemented method according to the present invention. Starting with a query vector for a spectrum of an unknown feedstuff raw material and/or feedstuff, the similarity values are calculated for each database vector of a population of spectra of known feedstuff raw materials and/or feedstuffs. The thus obtained similarity values are ordered either ascending, with the highest at the top, if similarity values were calculated with a similarity measure, or descending, with the lowest at the top, if similarity values were calculated with a distance measure, to give a ranking. The top-n ranked vectors, which represent the nearest neighbors to the query vectors in the similarity search, are selected from this ranking and the occurrences of the corresponding classes, i.e. of the feedstuff raw materials and/or feedstuffs, are determined. Said classes are weighted according to the rank of their vectors and added up to give class scores. The class scores are ranked according to the values with the highest value at the top. The feedstuff raw material and/or feedstuff of the top-ranked class has the highest similarity with the query vector and therefore, it is assigned to the sample of the query vector.

EXAMPLE

The following is an example to illustrate the computer-implemented method according to the present invention in comparison to a simple prediction method of the prior art, and a prediction method involving a majority voting.

In the first step, the NIR spectrum of a sample of the feedstuff raw material FRM3 was recorded. The relevant information of said spectrum, i.e. absorption intensities of wavelengths, were transformed to give a query vector of said spectrum. In the next step, the similarity values of all database vectors with the query vector were calculated using a distance measure. The thus obtained similarity values were ranked according to their values including the indication of their corresponding feedstuff raw material and/or feedstuff in descending order to give a ranking of the database vector.

In the simple prediction model according to the prior art (in the following also referred to as Prediction method 1: 1-NN), the top-n vectors in this ranking represented the nearest neighbors in the similarity analysis between the query vector of the sample of an unknown feedstuff raw material and/or unknown feedstuff and the database vectors of a population of spectra of known feedstuff raw materials and/or feedstuffs.

The method with majority voting also started from the ranking of the database as mentioned above but also involves a counting of the occurrences of the material cases, i.e. the feedstuff raw material and/or feedstuff corresponding to the database vectors.

Finally, the method according to the present invention was used, which involves a majority-voting and a weighting of the thus obtained results.

12

TABLE 1

| Ranking of database vectors according to their ranking and stating their corresponding type feedstuff raw material and/or feedstuff, i.e. FRM1. FRM2 or FRM3. | | | |
| --- | --- | --- | --- |
| Rank | Similarity value | Vector name | Feedstuff raw material/feedstuff |
| 1 | 0.93 | V1 | FRM1 |
| 2 | 0.91 | V3 | FRM3 |
| 3 | 0.74 | V5 | FRM3 |
| 4 | 0.69 | V4 | FRM3 |
| 5 | 0.42 | V7 | FRM2 |
| 6 | 0.33 | V2 | FRM3 |
| 7 | 0.27 | V12 | FRM2 |
| 8 | 0.15 | V6 | FRM2 |
| 9 | 0.04 | V8 | FRM1 |
| 10 | 0.03 | V9 | FRM1 |
| 11 | 0.02 | V10 | FRM2 |
| 12 | 0.01 | V11 | FRM2 |

In the prediction method 1 (1-NN) the feedstuff raw material with the highest similarity value according to the rankling of Table 1, i.e. FRM1, is indicated as the feedstuff raw material with the highest similarity to the material of the query vector.

By comparison, in the prediction method 2 (majority voting), the feedstuff raw material with the greatest number of occurrences in the ranking of Table 1, i.e. FRM2 with 5 votings over FRM1 with 3 votings and FRM2 with 4 votings, is indicated as the feedstuff raw material with the highest similarity to the material of the query vector.

In the prediction method 3. i.e. the method according to the present invention, the feedstuff raw material FRM3 is indicated as the feedstuff raw material with the highest similarity to the material of the query vector.

$$FRM3 \rightarrow \frac{1}{2}+\frac{1}{3}+\frac{1}{4}+\frac{1}{6}=1.249$$

$$FRM2 \rightarrow \frac{1}{5}+\frac{1}{7}+\frac{1}{8}+\frac{1}{11}+\frac{1}{12}=0.640$$

$$FRM1 \rightarrow \frac{1}{1}+\frac{1}{9}+\frac{1}{10}=1.211$$

The results of the three methods are extremely different. More importantly, two of the tested methods also give false positive results. Only the method according to the present invention gave the correct result.

The invention claimed is:

1. A computer-implemented method for predicting a feedstuff and/or feedstuff raw material, the method comprising:
   a) providing a near infrared (NIR) spectrum of a sample of an unknown feedstuff raw material and/or feedstuff;
   b) transforming absorption intensities of wavelengths or wavenumbers in the spectrum of step a) to give a query vector;
   c) providing a set of database vectors of a population of spectra of known feedstuff raw materials and/or feedstuffs, wherein the population of spectra of known feedstuffs and/or feedstuff raw materials comprises at least 50 spectra of samples of each feedstuff and/or feedstuff raw material from each of its global growing areas;
   d) analyzing the similarity between the query vector of step b) and the set of database vectors of step c), the analyzing comprising:
   d1) calculating a similarity measure and a distance measure between each database vector of step c) and the query vector of step b) to give a similarity value for each database vector with the query vector;
   d2) ranking the similarity values obtained in step d1) in descending order, when the similarity measure is calculated in step d1) or in ascending order, when the distance measure is calculated in step d1), wherein the top-ranked database vector has the greatest similarity with the query vector;

d3) counting a number of occurrences of each of the feedstuff raw materials and/or feedstuffs among the top-ranked database vectors in the ranking of step d2), wherein the number of occurrences is indicated by the variable N per each feedstuff raw material and/or feedstuff;

d4) weighting the first N similarity values of each of the feedstuff raw materials and/or feedstuffs according to their position in the ranking of step d2) to give weighted rank positions of each of the feedstuff raw materials and/or feedstuffs, wherein the weighting of similarity values is done by taking the reciprocal rank position of the feedstuff raw material and/or feedstuff in ranking of step d2); and d5) forming the sum of the weighted rank positions of step d4) for each of the feedstuff raw materials and/or feedstuffs to give scores of each of the feedstuff raw materials and/or feedstuffs;

and e) assigning the feedstuff raw material and/or feedstuff of the database vector with the highest score to the sample of step a), wherein the distances of the absorption intensities being transformed to vectors in step b) are identical with the distances of the absorptions intensities transformed to vectors in step c), wherein the vector in step b) and c) is a multi-dimensional vector, with each dimension of the vector corresponding to an absorption intensity of a specific wavelength or wavenumber, wherein a processing unit is configured to carry out the method of each of steps a), b), c), d), d1), d2), d3), d4), d5) and e),

wherein the processing unit forms a network with at least one other processing unit, on which the database vectors are stored, wherein a distance between the wavelengths in step b) is from 0.1 nm+/−10% to 2 nm +/−10%, and wherein a distance between wavelengths in step c) are the same as the distance in step b).

2. The method of claim 1, wherein the spectrum in step a) and/or in step c) is recorded in a range of from 1,100 to 2,500 nm.

3. The method of claim 1, wherein the absorption intensities of equidistant wavelengths and/or wavenumbers in a spectrum are transformed to give a vector of a spectrum of step a) and/or of step b).

4. The method of claim 1, wherein a number of the top-ranked database vectors to be considered in step d3) ranges from 10 to 100.

5. The method of claim 1, wherein a number of the top-ranked database vectors to be considered in step d3) ranges from 10 to 50.

6. The method of claim 1, wherein the population of spectra of known feedstuffs and/or feedstuff raw materials in step c) comprises spectra of all feedstuffs and/or feedstuff raw materials in ground and/or unground form used in animal nutrition.

7. The method of claim 1, further comprising forming a derivative of the spectrum of the unknown feedstuff raw material and/or feedstuff of step a) and/or of the spectra of known feedstuff raw materials and/or feedstuffs of step c).

8. The method of claim 7, further comprising forming a second derivative of the spectrum of the unknown feedstuff raw material and/or feedstuff of step a) and/or of the spectra of known feedstuff raw materials and/or feedstuffs of step c).

* * * * *